(12) United States Patent
Cima et al.

(10) Patent No.: US 6,530,958 B1
(45) Date of Patent: Mar. 11, 2003

(54) TISSUE REGENERATION MATRICES BY SOLID FREE-FORM FABRICATION TECHNIQUES

(75) Inventors: Linda G. Cima, Lexington, MA (US); Michael J. Cima, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 08/463,203

(22) Filed: Jun. 5, 1995

Related U.S. Application Data

(60) Division of application No. 08/200,636, filed on Feb. 23, 1994, now Pat. No. 5,510,680, which is a continuation-in-part of application No. 08/138,345, filed on Oct. 18, 1993, now Pat. No. 5,490,962.

(51) Int. Cl.[7] .................................................. A61F 2/28
(52) U.S. Cl. ................................ 623/23.51; 623/23.57; 623/23.61; 623/901
(58) Field of Search .......................... 623/11.11, 23.56, 623/23.51, 23.58, 23.61, 23.57, 901, 911; 264/401

(56) References Cited

U.S. PATENT DOCUMENTS

| 4,060,081 A | 11/1977 | Yannas et al. | |
|---|---|---|---|
| 4,485,097 A | 11/1984 | Bell | |
| 4,520,821 A | 6/1985 | Schmidt | |
| 4,609,551 A | 9/1986 | Caplan | |
| 4,620,327 A | * 11/1986 | Caplan et al. | 623/10 |
| 4,787,900 A | 11/1988 | Yannas et al. | 623/1 |
| 4,846,838 A | * 7/1989 | Takai et al. | 623/66 |
| 4,927,632 A | 5/1990 | Wong | 424/422 |
| 4,985,036 A | 1/1991 | Lommen et al. | 623/15 |
| 5,011,692 A | 4/1991 | Fujioka et al. | 424/426 |
| 5,059,123 A | 10/1991 | Jernberg | 433/215 |
| 5,171,261 A | 12/1992 | Noishiki et al. | 623/1 |
| 5,197,985 A | 3/1993 | Caplan | |
| 5,204,055 A | * 4/1993 | Sachs et al. | 419/2 |
| 5,226,914 A | 7/1993 | Caplan | |
| 5,260,009 A | 11/1993 | Penn | 264/40.1 |
| 5,338,772 A | 8/1994 | Bauer et al. | 523/115 |
| 5,348,788 A | * 9/1994 | White | 623/11 |
| 5,370,692 A | * 12/1994 | Fink et al. | 623/66 |
| 5,447,724 A | 9/1995 | Helmus et al. | 424/426 |
| 5,460,758 A | 10/1995 | Langer et al. | 264/401 |
| 5,466,462 A | 11/1995 | Rosenthal et al. | 424/426 |
| 5,490,962 A | * 2/1996 | Cima et al. | 264/22 |
| 5,496,372 A | * 3/1996 | Hamamotot et al. | 623/16 |
| 5,510,066 A | 4/1996 | Fink et al. | 264/40.1 |
| 5,518,680 A | * 5/1996 | Cima et al. | 264/401 |

FOREIGN PATENT DOCUMENTS

DE   41 02 259 A1   7/1992

OTHER PUBLICATIONS

Boeree, N.R., et al., "Development of a Degradable Composite for Orthopedic Use: Mechanical Evaluation of an Hydroxyapatite Polyhydroxygutyrate Composite Material," *BioMaterials*, 14 793–796 (1993).

Martin, R.B., et al., "Bone Ingrowth and Mechanical Properties of Coralline Hydroxyapatite One Year After Implantation," *BioMaterials*, 14, 341–348 (1993).

Sachs, et al., "CAD–Casting: Direct Fabrication of Ceramic Shells and Cores by Three Dimensional Printing," *Review*, 5(2), 117–126 (1992).

Vacanti, et al., "Selective Cell Transplation Using Bioabsorbable Artificial Polymers as Matrices," Journal of Pediatric Surgery, vol. 23, No. 1, (1–1988) pp. 3–9.

* cited by examiner

*Primary Examiner*—Paul B. Prebilic
(74) *Attorney, Agent, or Firm*—Holland & Knight LLP

(57) ABSTRACT

Solid free-form (SSF) techniques for making medical devices for implantation and growth of cells from polymers or polymer/inorganic composites using computer aided design are described. Examples of SFF methods include stereo-lithography (SLA), selective laser sintering (SLS), ballistic particle manufacturing (BPM), fusion deposition modeling (FDM), and three dimensional printing (3DP). The devices can incorporate inorganic particles to improve the strength of the walls forming the pores within the matrix and to provide a source of mineral for the regenerating tissue. The devices can contain tissue adhesion peptides, or can be coated with materials which reduce tissue adhesion. The macrostructure and porosity of the device can be manipulated by controlling printing parameters. Most importantly, these features can be designed and tailored using computer assisted design (CAD) for individual patients to optimize therapy.

15 Claims, No Drawings

TISSUE REGENERATION MATRICES BY SOLID FREE-FORM FABRICATION TECHNIQUES

This is a divisional of U.S. Ser. No. 08/200,636 filed Feb. 23, 1994, now U.S. Pat. No. 5,510,680, which is a continuation in part of U.S. Ser. No. 08/138,345 entitled "Preparation of Medical Devices by Solid Free-Form Fabrication Methods" filed Oct. 18, 1993 by Linda G. Cima and Michael J. Cima, issued as U.S. Pat. No. 5,490,962.

The government has certain rights in this invention by virtue of Grant Number DDM-8913977 awarded by the National Science Foundation.

BACKGROUND OF THE INVENTION

The present invention is in the area of methods for formulating devices for tissue regeneration, which uses computer-aided design (CAD) in combination with solid free-form fabrication technology.

Strategies for regenerating tissue are being developed in response to a range of clinical needs, including replacement of damaged or genetically absent metabolic function from tissues such as liver, pancreas and pituitary tissue, and repair or restructuring of damaged or malformed connective tissues such as bone, cartilage and skin. Unlike blood or bone marrow tissues which can be regenerated by intravenous injection of cells, regeneration of most tissues requires a template to guide their growth.

New therapies for tissue regeneration include approaches in which cells are transplanted into a patient along with a device, and approaches in which a device is implanted next to normal tissue and guides the growth of that tissue into a new region. An example of the latter is a bone regeneration device placed into a fracture site, which guides growth of bone tissue into the fracture.

A number of approaches have been described for fabricating tissue regeneration devices for either in vitro or in vivo growth of cells. Polymeric devices have been described for replacing organ function or providing structural support. Such methods have been reported by Vacanti, et al., *Arch. Surg.* 123, 545–549 (1988), U.S. Pat. No. 4,060,081 to Yannas, et al., U.S. Pat. No. 4,485,097 to Bell, and U.S. Pat. No. 4,520,821 to Schmidt, et al. In general, however, the methods used by Vacanti, et al., and Schmidt, et al., can be practiced by selecting and adapting existing polymer fiber compositions for implantation and seeding with cells, while the methods of Yannas and Bell produce very specific modified collagen sponge-like structures.

Various materials are used to fabricate inorganic or inorganic/polymer matrices for bone regeneration. These include the coralline replaniform hydroxyapatite, which is essentially an adapted coral as described by Martin, R. B., et al., "Bone ingrowth and mechanical properties of coralline hydroxyapatite one year after implantation," *Biomaterials*, 14:341–348 (1993), and devices which incorporate a cellular component, as described by U.S. Pat. Nos. 4,620,327, 4,609,551, 5,226,914 and 5,197,985 to Arnold Caplan. Composite materials have also been described; however, they have been used primarily for fixation devices, and not bone ingrowth. See, for example, Boeree, N. R., et al., "Development of a degradable composite for orthopedic use: mechanical evaluation of an hydroxyapatite-polyhydroxybutyrate composite material," *Biomaterials*, 14:793–796 (1993).

Tissue regeneration devices must be porous with interconnected pores to allow cell and tissue penetration. Factors such as pore size, shape and tortuosity can all affect tissue ingrowth but are difficult to control using standard processing techniques.

It would be advantageous to construct specific structures from biocompatible synthetic or natural polymers, inorganic materials, or composites of inorganic materials with polymers, where the resulting structure has defined pore sizes, shapes and orientations, particularly different pore sizes and orientations within the same device, with more than one surface chemistry or texture at different specified sites within the device.

It is therefore an object of the present invention to provide methods and compositions for the preparation of complex, temporal and spatial patterns for use in tissue regeneration.

It is another object of the present invention to provide methods and compositions for making complex medical devices of bioerodible or non-bioerodible materials or composites for either cell transplantation or matrix-guided tissue regeneration.

It is a further object of the present invention to provide methods that operate with high precision and reproducibility to produce medical devices.

It is a still further object of the present invention to produce devices which can selectively encourage the growth of one tissue type over another at specific sites within the matrix by virtue of control of surface chemistry and texture or growth factor release at that region of the matrix.

SUMMARY OF THE INVENTION

Solid free-form fabrication (SFF) methods are used to manufacture devices for allowing tissue regeneration and for seeding and implanting cells to form organ and structural components, which can additionally provide Controlled release of bioactive agents. The SFF methods can be adapted for use with a variety of polymeric, inorganic and composite materials to create structures with defined compositions, strengths, and densities, using computer aided design (CAD).

Examples of SFF methods include stereo-lithography (SLA), selective laser sintering (SLS), ballistic particle manufacturing (BPM), fusion deposition modeling (FDM), and three dimensional printing (3DP). In a preferred embodiment, 3DP is used to precisely create channels and pores within a matrix to control subsequent cell growth and proliferation in the matrix. For example, 3DP can be used to create a porous bioerodible matrix having interconnected pores or channels, typically between 0.15 and 0.5 mm, which are separated by walls approximately 30 to 100 microns thick, which have an average pore size of approximately 5 to 40 microns.

The macrostructure and porosity of the device can be manipulated by controlling printing parameters, the type of polymer and particle size, as well as the solvent and/or binder. Porosity of the matrix walls, as well as the matrix per se, can be manipulated using SFF methods, especially 3DP. Structural elements that maintain the integrity of the devices during erosion can also be incorporated. For example, to provide support, the walls of the device can be filled with resorbable inorganic material, which can further provide a source of mineral for the regenerating tissue. Most importantly, these features can be designed and tailored using computer assisted design (CAD) for individual patients to individualize the fit of the device.

DETAILED DESCRIPTION OF THE INVENTION

Solid free-form fabrication methods offer several advantages for constructing medical devices for tissue engineering. Devices for tissue regeneration can be constructed to fit the individual patient, individual cell type or organ structure. The device can include a specified bioactive agent composition gradient and structure to deliver drugs to the site of regeneration, and can be tailored to the needs of individual patients. SFF methods can be used to selectively control the composition within the build plane by varying the composition of printed material. Unconventional microstructures, such as those with complicated porous networks or unusual composition gradients, can be designed at a CAD terminal and built through an SFF process such as 3DP. Complex resorbable or erodible medical devices can be built which incorporate structural elements to insure the structural integrity of the device during erosion.

EXAMPLES OF USEFUL SFF PROCESSES

Three Dimensional Printing (3DP)

3DP is described by Sachs, et al., "CAD-Casting: Direct Fabrication of Ceramic Shells and Cores by Three Dimensional Printing" *Manufacturing Review* 5(2), 117–126 (1992) and U.S. Pat. No. 5,204,055 to Sachs, et al., the teachings of which are incorporated herein. Suitable devices include both those with a continuous jet stream print head and a drop-on-demand stream print head. A high speed printer of the continuous type, for example, is the Dijit printer made and sold by Diconix, Inc., of Dayton, Ohio, which has a line printing bar containing approximately 1,500 jets which can deliver up to 60 million droplets per second in a continuous fashion and can print at speeds up to 900 feet per minute. Both raster and vector apparatuses can be used. A raster apparatus is where the printhead goes back and forth across the bed with the jet turning on and off. This can have problems when the material is likely to clog the jet upon settling. A vector apparatus is similar to an x-y printer. Although potentially slower, the vector printer may yield a more uniform finish.

3DP is used to create a solid object by ink-jet printing a binder into selected areas of sequentially deposited layers of powder. Each layer is created by spreading a thin layer of powder over the surface of a powder bed. The powder bed is supported by a piston which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three dimensional structure. The unbound powder supports temporarily unconnected portions of the component as the structure is built but is removed after completion of printing.

As shown in U.S. Pat. No. 5,204,055, the 3DP apparatus includes a powder dispersion head which is driven reciprocally in a shuttle motion along the length of the powder bed. A linear stepping motor assembly is used to move the powder distribution head and the binder deposition head. The powdered material is dispensed in a confined region as the dispensing head is moved in discrete steps along the mold length to form a relatively loose layer having a typical thickness of about 100 to 200 microns, for example. An ink-jet print head having a plurality of ink-jet dispensers is also driven by the stepping motor assembly in the same reciprocal manner so as to follow the motion of the powder head and to selectively produce jets of a liquid binder material at selected regions which represent the walls of each cavity, thereby causing the powdered material at such regions to become bonded. The binder jets are dispensed along a line of the printhead which is moved in substantially the same manner as the dispensing head. Typical binder droplet sizes are between about 15 to 50 microns in diameter. The powder/binder layer forming process is repeated so as to build up the device layer by layer.

While the layers become hardened or at least partially hardened as each of the layers is laid down, once the desired final part configuration is achieved and the layering process is complete, in some applications it may be desirable that the form and its contents be heated or cured at a suitably selected temperature to further promote binding of the powder particles. In either case, whether or not further curing is required, the loose, unbonded powder particles are removed using a suitable technique, such as ultrasonic cleaning, to leave a finished device.

Construction of a 3DP component can be viewed as the knitting together of structural elements that result from printing individual binder droplets into a powder bed. These elements are called microstructural primitives. The dimensions of the primitives determine the length scale over which the microstructure can be changed. Thus, the smallest region over which the concentration of bioactive agent can be varied has dimensions near that of individual droplet primitives. Droplet primitives have dimensions that are very similar to the width of line primitives formed by consecutive printing of droplets along a single line in the powder bed. The dimensions of the line primitive depend on the powder and the amount of binder printed per unit line length. A line primitive of 500 $\mu$m width is produced if an ink jet depositing 1.1 cc/min of methylene chloride is made to travel at 8"/sec over the surface of a PLC powder bed with between approximately 45 to 75 $\mu$m particle size. Higher print head velocities and smaller particle size produce finer lines. The dimensions of the primitive seem to scale with that calculated on the assumption that the liquid binder or solvent needs to fill the pores of the region in the powder which forms the primitive.

Finer feature size is also achieved by printing polymer solutions rather than pure solvents. For example, a 10 wt % PLC solution in chloroform produces 200 $\mu$m lines under the same conditions as above. The higher solution viscosity prevents slows the migration of solvent away from the center of the primitive.

The solvent drying rate is an important variable in the production of polymer parts by 3DP. Very rapid drying of the solvent tends to cause warping of the printed component. Much, if not all, of the warping can be eliminated by choosing a solvent with a low vapor pressure. Thus, PCL parts prepared by printing chloroform have nearly undetectable amounts of warpage, while large parts made with methylene chloride exhibit significant warpage. It has been found that it is often convenient to combine solvents to achieve minimal warping and adequate bonding between the particles. Thus, an aggressive solvent can be mixed in small proportions with a solvent with lower vapor pressure.

Stereo-lithography (SLA) and Selective Laser Sinterina (SLS)

SFF methods are particularly useful for their ability to control composition and microstructure on a small scale for the construction of these medical devices. The SFF methods, in addition to 3DP, that can be utilized to some degree as described herein are stereo-lithography (SLA), selective laser sintering (SLS), ballistic particle manufacturing (BPM), and fusion deposition modeling (FDM).

Stereolithography is based on the use of a focused ultraviolet (UV) laser which is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired device is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biocompatible polymeric materials.

SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTH Corporation of Austin, Tex.

SLA and SLS are thus similar in that in both techniques, matter is laminated to make three dimensional shapes. Use of these methods to control composition is limited to one dimensional control since one can only vary the composition of each layer. Nonetheless, these methods can be useful for construction of drug delivery and tissue matrix devices where one dimensional compositional control is all that is desired or where only variation in porosity is desired. Controlled porosity can be built using SLA and SLS simply by specifying the laser path over the layer surface to include only those regions which are to remain in the device.

However, SLA and SLS pose significant material constraints for the construction of tissue matrix preforms. SLA is limited to use with a photopolymerizable precursor that yields a biocompatible solid, such as UV or visible light curable acrylic systems used for bioadhesives, or a photo-curable material such as polyethylene oxide (PEO) precursors terminated with photo-crosslinking end groups. This process can be performed in the presence of sensitive biomolecules. Thus, structures can be built that incorporate drugs. Secondly, variation of the laser intensity or traversal speed can be used to vary the cross-link density within a layer so that the properties of the material can be varied from position to position with the part. SLS has the disadvantage that incorporation of sensitive biomolecules is difficult because of the need to locally heat the powder layer so as to sinter it. Nonetheless, highly porous structures can be built with low melting polymers, such as PEO powder. Variation of the laser intensity or traversal speed controls the degree of local densification. Thus, regions where the laser intensity is high or the traversal speed is low will have higher density.

Ballistic Particle Manufacturing (BPM) and Fusion Deposition Modeling (FDM)

BPM uses an ink-jet printing apparatus wherein an ink-jet stream of liquid polymer or polymer composite material is used to create three-dimensional objects under computer control, similar to the way an ink-jet printer produces two-dimensional graphic printing. The device is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y.

FDM employs an x-y plotter with a z motion to position an extrudable filament formed of a polymeric material, rendered fluid by heat or the presence of a solvent. A suitable system is available from stratasys, Incorporated of Minneapolis, Minn.

BPM, FDM and 3DP are related in the sense that all three approaches deposit matter in small areas. Thus, they offer the advantage that local composition can be specified and constructed for any desired three dimensional profile. The composition control is only limited by the resolution of the particular apparatus used for construction. FDM builds structures by extruding a fine filament of plastically deformable material through a small nozzle. The nozzle is directed over the built surface by appropriate x, y and z motion control so as to yield the desired three dimensional structure. Similarly, BPM involves motion control of an ink jet print head to deposit matter in the form of small droplets. Appropriate control of where the droplets are printed permits the construction of a desired three dimensional shape. 3DP uses two sources of material: the material that makes up the porous layer and the material that is printed.

Local composition control using FDM and BPM requires the application of multiple printing or extrusion tools. A similar approach can be followed with 3DP by using multiple print-heads. Alternatively, multiple droplets may be printed into the same location when using 3DP to increase the local composition of the species contained in the printed solution.

Porosity control using BPM and FDM can be accomplished using procedures similar to those which can be practiced using 3DP, as described below.

Selection of Polymers

Depending on the processing method, the polymer forming the matrix may be in solution, as in the case of SLA, or in particle form, as in the case of SLS, BPM, FDM, and 3DP. In the first method, the polymer must be photopolymerizable. In the latter methods, the polymer is preferably in particulate form and is solidified by application of heat, solvent, or binder (adhesive). In the case of SLS and FDM, it is preferable to select polymers having relatively low melting points, to avoid exposing incorporated bioactive agent to elevated temperatures.

In the case of 3DP, a polymeric material, preferably in particulate form, or as a porous sheet, is applied to a solid platform on a movable piston for solidification and/or incorporation of bioactive agent. A roller evenly spreads the particles over the platform bed. Solvent and/or binder and bioactive agent is then selectively printed onto the polymer particles. After each layer is "printed", the piston lowers the polymeric material so that the process can be repeated to form the next layer.

The particles can be of any shape, including fibrous or rod shaped, although a more spherical particle will typically flow more smoothly. The particles are preferably in the range of ten microns or greater in diameter, although smaller particles can be used if spread in a liquid medium and allowed to dry in between printings.

A number of materials are commonly used to form a matrix. Unless otherwise specified, the term "polymer" will be used to include any of the materials used to form the bioactive agent matrix, including polymers and monomers which can be polymerized or adhered to form an integral unit. In a preferred embodiment the particles are formed of a polymer, such as a synthetic thermoplastic polymer, for example, ethylene vinyl acetate, poly(anhydrides), polyorthoesters, polymers of lactic acid and glycolic acid and other a hydroxy acids, and polyphosphazenes, a protein polymer, for example, albumin or collagen, or a polysaccharide containing sugar units such as lactose. The polymer can be non-biodegradable or biodegradable, typically via hydrolysis or enzymatic cleavage. Non-polymeric materials can also be used to form the matrix and are included within the term "polymer" unless otherwise specified. Examples include organic and inorganic materials such as hydoxyapatite, calcium carbonate, buffering agents, and lactose, as well as other common excipients used in drugs, which are solidified by application of adhesive rather than solvent. In the case of polymers for use in making devices for cell attachment and growth, polymers are selected based on the ability of the polymer to elicit the appropriate biological response from cells, for example, attachment, migration, proliferation and gene expression.

Photopolymerizable, biocompatible water-soluble polymers include polyethylene glycol tetraacrylate (Ms 18,500) which can be photopolymerized with an argon laser under biologically compatible conditions using an initiator such as triethanolamine, N-vinylpyrrolidone, and eosin Y. Similar photopolymerizable macromers having a poly(ethylene glycol) central block, extended with hydrolyzable oligomers such as oligo(d,l-lactic acid) or oligo(glycolic acid) and terminated with acrylate groups, may be used.

Examples of biocompatible polymers with low melting temperatures include polyethyleneglycol 400 which melts at 4–8° C., PEG 600 which melts at 20–25° C., and PEG 1500 which melts at 44–48° C. another low melting material is stearic acid, which melts at 70° C.

Other suitable polymers can be obtained by reference to The Polymer Handbook, 3rd edition (Wiley, N.Y. 1989), the teachings of which are incorporated herein.

A preferred material is a polyester in the polylactide/polyglycolide family. These polymers have received a great deal of attention in the drug delivery and tissue regeneration areas for a number of reasons. They have been in use for over 20 years in surgical sutures, are Food and Drug Administration (FDA)-approved and have a long and favorable clinical record. A wide range of physical properties and degradation times can be achieved by varying the monomer ratios in lactide/glycolide copolymers: poly-L-lactic acid (PLLA) and poly-glycolic acid (PGA) exhibit a high degree of crystallinity and degrade relatively slowly, while copolymers of PLLA and PGA, PLGAs, are amorphous and rapidly degraded. Although attempts have been made to develop true surface-eroding polymer, for example, polyanhydrides, the relationship between polymer composition and device properties are very difficult to control in practice by standard fabrication techniques. These problems are avoided using the processing technology described herein.

Selection of Binder

Solvents and/or binder are used in the preferred method, 3DP, as well as SLA and BPM.

The binder can be a solvent for the polymer and/or bioactive agent or an adhesive which binds the polymer particles. Solvents for most of the thermoplastic polymers are known, for example, methylene chloride or other organic solvents. Organic and aqueous solvents for the protein and polysaccharide polymers are also known, although an aqueous solution is preferred if denaturation of the protein is to be avoided. In some cases, however, binding is best achieved by denaturation of the protein.

The binder can be the same material as is used in conventional powder processing methods or may be designed to ultimately yield the same binder through chemical or physical changes that take place in the powder bed after printing, for example, as a result of heating, photopolymerization, or catalysis.

The selection of the solvent for the bioactive agent depends on the desired mode of release. In the case of an erodible device, the solvent is selected to either dissolve the matrix or is selected to contain a second polymer which is deposited along with the drug. In the first case, the printed droplet locally dissolves the polymer powder and begins to evaporate. The drug is effectively deposited in the polymer powder after evaporation since the dissolved polymer is deposited along with the drug. The case where both the drug and a polymer are dissolved in the printed solution is useful in cases where the powder layer is not soluble in the solvent. In this case, binding is achieved by deposition of the drug polymer composite at the necks between the powder particles so that they are effectively bound together.

Aggressive solvents tend to nearly dissolve the particles and reprecipitate dense polymer upon drying. The time for drying is primarily determined by the vapor pressure of the solvent. There is a range from one extreme over which the polymer is very soluble, for example, 30 weight percent solubility, which allows the polymer to dissolve very quickly, during the time required to print one layer, as compared with lower solubilities. The degree to which the particles are attacked depends on the particle size and the solubility of the polymer in the solvent. Fine powder is more completely dissolved than powder with larger particle size.

Binders and Polymer Concentration

The binder can be a resorbable polymer such as polylactic acid or polycaprolactone of molecular weight 50,000–200,000, in a solvent such as chloroform or a mixture of chloroform and a less-volatile solvent such as ethyl acetate to minimize warping.

The polymer concentration in the binder solution will generally be at the limit of what can be accommodated by the nozzle, both to maximize the amount of matter delivered and to minimize migration of the solvent away from the ballistic impact point of the drop, thereby maximizing the resolution of the line width. The upper limit of polymer concentration is 15% for poly-L-lactic acid of 100,000 MW. This concentration of polymer may in some cases be insufficient in one-pass printing; devices made with larger powders may be cohesive with this amount of polymer. The amount of matter printed can be increased by including small latex or other particles in the printing solution. For example, polyglycolic acid (PGA) is not soluble in chloroform or ethyl acetate. Nanoparticles of PGA could be included in the printing solution (particles up to microns in diameter can be accommodated through the nozzle) to increase the polymer content which is printed. Latexes containing 30% by weight polymer (Eudragitυ are commercially available acrylic latexes) have been printed in existing machines without complications.

The amount of matter which is printed into the bed can also be increased by including small inorganic particles in the polymer solution, for example, bone derive apatite.

Another approach to increasing the amount of polymer printed in the bed is to print a second or more passes after the first pass has dried before moving to the next layer.

Means for Altering Texture of Device Features

A "wall", for example, a feature 100 microns thick by 1 cm×1 cm, will exhibit different textures if it is built by printing a single line layer after layer after layer up through the depth of the bed, as compared to printing a sheet of contiguous lines within one layer. The wall built up by printing a line layer after layer will have texture on both sides (some of the powder will adhere), and that texture will be identical on each side. In contrast, a sheet printed using contiguous lines within the same layer will in most cases have different textures on each side. The "bottom" will have a texture influenced by incomplete assimilation of the powder into the bulk of the polymer wall. The "top" can be smooth, because more binder is inherently trapped in the top of the printed line, covering up the particles. However, at low polymer concentrations in the printed binder, the top of the "sheet" can also exhibit significant texture since the binder is less viscous and can penetrate into the powder more easily.

The texture in a sheet is influenced both by the binder concentration in the powder and by the spacing between contiguous lines. For example, a 15% PCL solution in chloroform printed into PCL powder with 75–100 micron powder size using a printing speed of 4–12 cm/s will form a smooth layer if printed at a spacing of 25 microns but will form a highly textured surface if printed at a spacing of 75 microns.

These effects of texture can be beneficial in designing devices to get optimal tissue regeneration rates. A single channel of square cross-section can have smooth surfaces on one or two sides and textured surfaces on the other. Smooth surfaces can allow rapid cell migration, while textured surfaces can provide a site for cells to differentiate.

Formation of Composite Devices

Composite devices can be made by combining inorganic and organic components. In particular, it may be desired to increase the amount of polymer in the device above that which can be obtained by one-pass printing of a polymer solution into an inorganic powder bed, for example, by adding a polymer latex to the printing solution. Another method is to mix a polymer powder with an inorganic powder. Still another method is to spread only polymer powder in the bed, and print a dispersion of inorganic particles (up to 30 vol %) in a solvent which will bind the polymer powder together. An example of this is to print a solution of apatite particles in chloroform onto a PLA powder bed. Alternatively one can include a polymer binder with an inorganic dispersion, for example by adding 30% by volume particles to a 5% by weight solution of PLA in chloroform. In the extreme, the bed could contain no material at all; both the inorganic and organic material could be printed through the nozzle.

Bioactive Agents Which Can be Incorporated

There are essentially no limitations on the bioactive agents that can be incorporated into the devices, although those materials which can be processed into particles using spray drying, atomization, grinding, or other standard methodology, or those materials which can be formed into emulsifications, microparticles, liposomes, or other small particles, and which remain stable chemically and retain biological activity in a polymeric matrix, are preferred. Bioactive agents also include compounds having principally a structural role, for example, hydroxyapatite crystals in a matrix for bone regeneration. The particles may have a size of greater than or less than the particle size of the polymer particles used to make the matrix.

Examples generally include proteins and peptides, nucleic acids, polysaccharides, nucleic acids, lipids, and non-protein organic and inorganic compounds, referred to herein as "bioactive agents" unless specifically stated otherwise. These materials have biological effects including, but not limited to, anti-inflammatories, antimicrobials, anti-cancer, antivirals, hormones, antioxidants, channel blockers, and vaccines. It is also possible to incorporate materials not exerting a biological effect such as air, radiopaque materials such as barium, or other imaging agents.

In a preferred embodiment for tissue regeneration matrices, cell growth, differentiation, and/or migration modulators are incorporated into specific regions of the device at the same level of resolution as the pores and channels. These materials are commercially available from suppliers such as Sigma Chemical Company, and have been extensively described in the literature.

Patterns for Incorporation of Bioactive Agent

There are two principle methods for incorporation of bioactive agents: as a dispersion within a polymeric matrix and as discrete units within a discrete polymeric matrix. In the first case, the bioactive agent is preferably applied in the polymer particle binder; in the second, the bioactive agent is applied in a non-solvent for the polymer particles.

In the case of SLA, bioactive material to be incorporated is dispersed into the liquid matrix material; in all other cases, bioactive material to be incorporated can be mixed with the particles, although this can result in a significant waste of the material in the case of SLS and 3DP; in these cases it is preferable to incorporate the bioactive material into the solvent or binder.

For example, the devices can be composed of particles of bioactive agent dispersed or embedded in a matrix of degradable polymer, such as PLA, PGA, and their copolymers (PLGAs). Implantation of the device is followed by slow hydrolysis and erosion of the polymer matrix. The release rate of bioactive agent is determined by the erosion rate of the polymer rather than just diffusion. Thus, the drug release rate can be controlled by the distribution of the drug throughout the matrix or by variation of the polymer microstructure so that the erosion rate varies with the position in the device. A drug concentration profile that is periodic with position away from the device surface will, for example, yield a drug release rate that is periodic in time as the polymer is eroded. The same effect could also be achieved by periodic variation in polymer composition or porosity.

Incorporating Structural Elements

Practical application of erodible devices is limited by the mechanical integrity of the device during the course of erosion. Real erodible devices do not decompose by simple surface limited reactions. Rather, the surface and bulk microstructure evolve during the course of erosion and alter the rate at which the drug is delivered. For example, oral erodible devices pit and break apart, which modifies the surface area exposed to the fluid and changes the rate at which drug is released. Resorbable polymer devices swell before hydrolysis which also causes nonlinear release of the drug.

Structural elements made using the same or different polymeric particles can be designed within the device to provide physical structural support during degradation so as to avoid many of the problems associated with erodible devices. 3DP is used to create structural elements within the device formed by the solidification of the polymer particles, for example, by deposition of areas or regions of a different polymeric material, such as regions of a non-degradable polymer within regions of a degradable polymer.

Controlling Porosity in Devices

Porosity in 3D printed devices can be created either at the level of the feature size (between 10 and 20 microns and greater) or at a sub-feature size level. At the level of the feature size, porosity is controlled by where the features are placed, and thus pore size and shape can vary in three dimensions.

Porosity at a subfeature size level can be created in a variety of ways.

(1) Printing a polymer solution onto a bed of particles which are not soluble in the polymer and which can be subsequently leached with a non-solvent for the polymer. In this case, the polymer which forms the device is printed onto a bed of particles such as salt, sugar, or polyethylene oxide. After the printing process is complete, the device is removed from the powder bed and placed in a nonsolvent for the polymer which will dissolve the particles. For example, polylactic acid in chloroform could be printed onto a bed of sugar particles, and the sugar can subsequently be leached with water.

(2) Printing a polymer solution onto a bed of particles which are partially soluble in the printed solvent. An example is printing a polylactic acid solution onto a bed of polyethylene oxide particles. This procedure may allow interpenetration of PEO into the surface of the PLA and improve surface properties of the final device. Following printing, the PEO can be leached with water.

(3) Printing a polymer solution onto a heated bed of polymer. An example is printing polylactic acid in chloroform onto a bed of PLA particles heated to 100° C. The boiling point of chloroform is 60° C., and it will thus boil on hitting the particle bed, causing a foam to form.

(4) Printing a polymer solution onto a bed containing a foaming agent.

(5) Printing with solvents which have only a small solubility for the powder. In this manner only a small amount of polymer is deposited at the necks between the particles leaving much of the original porosity in the powder bed. For example, PCL is only slightly soluble in acetone and acetone has a relatively high vapor pressure. Very little polymer is, therefore, dissolved before the solvent dries. Thus, the necks formed between the particles are small and the porosity of the resulting component is much like that of the original powder bed.

Devices Having Modified Surface Properties

Modifying surface properties in select regions of the device is also important and can be accomplished by printing a solution containing surface-active agents into the regions or lines in between where the binder is printed. As used herein, a "surface-active agent" may be an agent which promotes cell adhesion, such as an RGD peptide, or a material which inhibits cell adhesion, such as a surfactant, for example, polyethylene glycol or a Pluronic™ (polypropylene oxid-polyethylene oxide block copolymers).

The surface-active agent should in general be contained in a solvent immiscible with the solvent used to print the binder.

For example, it may be desirable to incorporate adhesion peptides such as the RGD adhesion peptide into certain channels (e.g., those for blood vessel ingrowth). An adhesion peptide, such as the peptide having a hydrophobic tail marketed by Telios (La Hoya, Calif.) as Peptite™, can be dissolved in water and printed into the "voids" using a second set of printing nozzles. Adding water, a relatively non-volatile solvent, can alter the kinetics of solvent removal from regions printed with binder. For example, adding water can slow solvent removal by occluding the surface area for evaporation, and can help decrease warpage. on contact with the polymer surface, the peptide will adsorb out of solution onto the polymer surface.

The surface can also be modified to prevent cellular adhesion. This may be desirable to prevent excessive soft connective tissue ingrowth into the device from the surrounding tissue, and can be accomplished, for example, by printing an aqueous solution of a pluronic™ (BASF) or poloxamer™ in the voids. The hydrophobic block of such copolymers will adsorb to the surface of the channels, with the hydrophilic block extending into the aqueous phase. Surfaces with adsorbed pluronics™ resist adsorption of proteins and other biological macromolecules. Other adhesion-preventing materials are described in Lee, J. H., J. Kopecek, et al., "Protein-resistant surfaces prepared by PEO-containing block copolymer surfactants." *J. Biomed. Mat. Res*, 23:351–368 (1989), the teachings of which are hereby incorporated by reference.

Printing the device with surface active agents while the "walls" of the device are still "wet" with organic solvent (such as chloroform) can enhance the adsorption of the adhesion-preventing material to the walls and can even allow the hydrophobic block to become blended into the surface, enhancing the stability of the resulting surface modification.

Constructing Preforms for Tissue Engineering

Regeneration of native tissue structures can occur by stimulation of growth of neighboring, healthy tissue (e.g., healing a defect in bone) or may require transplantation of cells from another site, using either the patient's own tissue or that of a tissue-matched donor (e.g., growth of a new cartilage structure for plastic surgery, replacement of liver). In either case, a device which serves as a scaffold or template to aid the growth of the new tissue is almost always necessary. The device can serve many functions, including: (1) as an immobilization site for transplanted cells, (2) formation of a protective space to prevent soft tissue prolapse into the wound bed and allow healing with differentiated tissue, (3) directing migration or growth of cells via surface properties of the device, and (4) directing migration or growth of cells via release of soluble molecules such as growth factors, hormones, or cytokines.

For the three applications described above, as well as for other applications in tissue regeneration which can be envisioned, 3DP offers at least three advantages over current technologies for processing biodegradable polymers: (1) tailored macroscopic shapes, (2) well-defined microstructure, which may include bimodal pore size distribution and directionally oriented pores and channels, and (3) incorporation of growth factors during manufacture in order to provide controlled release of factors at specific sites.

As used herein, "tissue" includes both soft tissues such as parenchymal tissue (liver, pancreas, intestine, etc.), blood vessels, skin, and connective tissues such as cartilage and bone.

Although matrix construction varies with each tissue type, the methods used for construction will typically be the same, optimized to create appropriate shapes and pore sizes. In general, interconnected pores or channels will extend from the exterior throughout the interior, typically between 0.15 and 0.5 mm in diameter, which are separated by walls approximately 30 to 100 microns thick, which are either solid or porous with an average pore size of approximately 5 to 40 microns.

Ideally, devices used for tissue regeneration will have a specific macroscopic shape which can be fashioned to the specific needs of a patient. For example, in mandibular replacement a missing piece of the jaw bone on one side of the patient will be fabricated to exactly match existing bone on the undamaged side by inputting an MRI image of the existing bone into the CAD program which fabricates the device. Further, the devices will ideally have a specific tailored microstructure of interconnected pores and channels for tissue ingrowth where the pores and channels are of precisely defined size, shape, surface chemistry and position within three dimensions. For example, in the case of bone ingrowth, there may be large longitudinal channels for bone and smaller transverse channels for ingrowth of blood vessels from the periosteal tissue.

The design of a bone regeneration device is described below in Example 1. Similar techniques for creating tailored microstructures with specific surface chemistries and textures can be applied to almost any type of tissue. Microstructures tailored to bone involve a composite of inorganic particulates and organic material in the final device, and are the most general. Matrices for regenerating other tissues, such as liver and cartilage, can be fabricated in a similar fashion using either inorganic powder or polymer powder in the bed. For microstructures tailored to soft tissues it is undesirable to have an inorganic powder as a component of the final device. However, printing a solution of a polymer such as PLA in chloroform onto an inorganic powder bed or onto a bed of mixed polymer/inorganic is a technique for creating increased porosity in the final device if a water-soluble inorganic powder such as sodium chloride is used.

For microstructures tailored to bone, inorganic powders in the final device increase the strength of the device and provide a source of minerals for the regenerating tissue. The strength requirements of soft tissues such as liver are substantially less than for bone, so greater void fractions in the final devices can be tolerated.

Although these devices can be created by any of the SFF techniques, the preferred method is 3DP. In one approach, an inorganic powder is spread in the bed. This powder will generally be some form of calcium phosphate or hydroxyapatite and can be derived from natural sources (i.e., isolated from animal bones) or synthetically created powder. If the powder is isolated from bone (for example, by grinding bone in a Glenn Mills Milling machine), it may not be strictly inorganic but may contain natural proteins and other biological macromolecules. The powder is preferably resorbable or biodegradable. The powder size controls the resolution of the wall thickness and the layer thickness. Powders less than 40 microns in diameter are preferred in order to obtain resolutions of less than 100 microns. Resolution is generally at least twice the dimension of the powder size. Very fine powders, typically less than one micron in diameter, may be spread into the bed as a solution which is then allowed to dry, or such powders can be formed into thin, generally between 100 and 200 micron thick, coherent, porous sheets by non-specific interactions in a separate step outside the 3DP machine, and the resulting sheets can be laid in the bed as each layer is built up as an alternative to the normal rolling and spreading operation. Bone derived apatite is an example of an inorganic powder which can be processed in this manner. Bone derived apatite has particles of average dimensions 0.003×0.009×0.04 microns.

After a first layer of powder is spread or placed in the bed of the SFF device, a binder is printed at those locations where it is desired to have walls. The places where no binder is printed become channels or voids when the powder is removed at the end of the process. For long-bone fracture repair devices, a preferred design is to have straight channels of approximately 60 to 300 microns in diameter with approximately 60 to 150 micron walls running the length of the device end-to-end to allow the neighboring bone to grow into the device, and transverse channels of approximately 60 to 100 microns in diameter which will allow ingrowth of blood vessels from the periosteal region. Although the transverse channels need not be as numerous as the longitudinal channels from the perspective of the need for blood vessels to grow in, the overall void fraction of the device should remain at greater than 80% It may be desirable to have transverse walls as thin as 100 microns. The outermost layer may also be designed to prevent excessive tissue ingrowth from the periosteal region, by limiting the number of internal channels which are accessible.

This embodiment is further illustrated by the following non-limiting example of a process for construction of a bone regeneration matrix using 3DP.

EXAMPLE 1

Production of a Bone Regeneration Matrix

This example describes the production of a rectangular device 2 cm×1 cm×1 cm, where it is desired to have the bone grow in the direction which is 2 cm long, and all other outer surfaces will be in contact with soft tissue. This can be built by printing:

1st layer:

Lines 100 microns wide spaced 300 microns center-to-center along the length of the 2 cm axis (each line is 200 microns in depth), for a total of 30 lines.

Triplets of 100 micron wide lines (i.e., three lines printed side by side) with 100 micron spacing in between printed along the 1-cm axis, for a total of 25 triplets, to decrease the number of channels accessible from the outside.

2nd layer:

Lines 100 microns wide spaced 300 microns center-to-center along the length of the 2-cm axis; these lines are 200 microns in depth and placed directly above the lines in the previous layer. The spaces between the lines will form the longitudinal channels.

3rd layer:

Lines 100 microns wide with 100 micron spacing printed along the 1 cm axis with 100 micron spacing in between; a 200 micron depth in all layers is assumed from here on; lines are printed on top of each of the outside lines in each triplet in the layer below. In this layer, the only binder printed along the 2-cm axis is printed on the 2 outermost lines; in these lines, binder is printed on top of regions where the transverse triplets intersect the outermost line; this is to prevent excessive tissue ingrowth from the side directions.

4th-(n−2)th layer: Same as layer 2.

5th-(n−1)th layer: Same as layer 3.

nth layer: Same as layer 1.

A device 1 cm thick would have approximately 50 layers.

An alternative to the embodiment described above is to rotate the axes in any direction in the bed so the longitudinal channels (2-cm direction), for example, are built up through the depth of the bed. This approach may be particularly desirable due to the effect of position in the bed on the texture an exposed surface assumes, as discussed above.

The device described above can be modified to encompass more complex architectural features and macroscopic shapes by varying the printing instructions. For example, some of the lines in the second layer could be single, some could be pairs, some could be triplets. A pair is two lines printed contiguous to each other within a single layer. A triplet is three lines printed contiguous to each other within a single layer.

Example 2

Construction of Composite Devices

In a significantly different embodiment, an exogenously fabricated polymer device is incorporated within the 3DP fabricated device. Examples of exogenously fabricated devices include strips of a microporous membrane which are incorporated into the center of the device to enhance angiogenesis by the "architecture-driven mode" described by Jim Brauker & coworkers (Baxter Corp., Round Lake, Ill.). Architecture-driven angiogenesis refers to the appearance of stable blood vessel ingrowth next to an implanted membrane device as a result of the microstructure of the membrane independent of membrane material as long as the material is nontoxic.

Microporous membranes with fibrous architectures and pores in the range of between approximately 5 to 8 microns are associated with vascularized fibrous capsules. In contrast, nonporous membranes or membranes with larger pores or with sheet-like rather than fibrous architectures are associated with a vascular fibrous capsules. Architecture-driven vascularity is believed to be brought about by cytokines secreted by macrophages which infiltrate the pores of the microporous membrane. Microporous membranes can therefore be used as angiogenesis factors to attract blood vessel ingrowth into a laminated macroporous device (two macroporous membranes glued onto the outer surfaces of the microporous "angiogenic" membrane).

For a bone regeneration device, the microporous membrane (200 microns thick is standard) can either replace an entire layer or a thin (0.3 cm×2 cm, for the device described above) strip can be placed in the center of a layer with normal powder in the remainder of the layer. Another method for generating this type of microstructure is by "spreading" short small-diameter (less than about three micron) fibers; however, this is technically more difficult.

Modifications and variations of the method and compositions described herein will be obvious to those skilled in the art from the foregoing detailed description. Such modifications and variations are intended to come within the scope of the appended claims.

We claim:

1. A medical device for tissue regeneration formed using a solid free-form fabrication method comprising a matrix of successive layers of biocompatible polymeric material having interconnected pores extending throughout the matrix suitable for seeding or ingrowth of cells wherein the method is three dimensional printing, comprising:
   a) spreading a first dispersion of a biocompatible polymer powder onto a bed,
   b) printing a layer comprising a second dispersion of biocompatible polymer in a solvent which binds the first biocompatible in a solvent which binds the first biocompatible polymer powder to the second biocompatible polymer at locations where it is desired to have walls, and
   c) repeating steps a and b until the desired matrix is made.

2. A medical device for bone regeneration formed using three dimensional printing comprising a matrix of successive layers of biocompatible composite material having interconnected pores extending throughout the matrix suitable for seeding or ingrowth of cells, having a pore size of at least five to forty microns in diameter
   wherein the method comprises
   a) spreading a first dispersion of a resorbable powder selected from the group consisting of calcium phosphate, hydroxyapatite, and calcium carbonate onto a bed,
   b) printing a layer comprising a second dispersion of biocompatible polymer or composite powder in a solvent which binds the first powder to the second biocompatible polymer or composite powder at locations where it is desired to have walls, and
   c) repeating steps a and b until the desired matrix is made.

3. The device of claim 1 or claim 2 wherein the powder size is less than 40 microns in diameter.

4. The device of claim 2 wherein the walls are less than 100 microns thick.

5. The device of claim 2 wherein the binder or biocompatible polymer is a resorbable polymer selected from the group consisting of polyhydroxyacids, polyorthoesters, polyanhydrides, and copolymers and blends thereof.

6. The device of claim 2 wherein the polymer or biocompatible polymer includes a biodegradable latex.

7. The device of claim 1 or claim 2 further comprising surface-active agents that are printed into the regions or lines of the powder bed in between where the binder or biocompatible polymer is printed.

8. The device of claim 2 wherein a surface of the polymer or composite material is modified with a surface active agent which prevents adhesion of cells.

9. The device of claim 2 wherein an exogenously fabricated device is incorporated into the matrix by printing layers of binder around the exogenously fabricated device.

10. The device of claim 2 wherein the composite or polymeric material includes a bioactive agent.

11. The device of claim 10 wherein the biocompatible material is polymeric particles and the bioactive agent is added to the polymeric particles and dispersed in the polymer layers.

12. The device of claim 10 wherein the bioactive agent is added to a solvent or binder for polymeric particles used to form the polymer layers.

13. The device of claim 12 wherein the solvent for the bioactive agent is not a solvent for the polymer, wherein three dimensional printing is used to form discrete regions of bioactive agent within a polymeric matrix.

14. The device of claim 2 that incorporates a non-biodegradable material into the device to form structural elements maintaining the integrity of the device when formed of a biodegradable material.

15. A rectangular device for bone regeneration of approximate size 2 cm×1 cm×1 cm, comprising:
   a) a first layer comprising:
      (i) lines approximately 100 microns wide spaced approximately 300 microns center-to-center along the length of the 2 cm axis, wherein each line is 200 microns in depth, totaling 30 lines, and (ii) triplets of approximately 100 micron wide lines with approximate 100 micron spacing in between printed along the 1-cm axis, for a total of 25 triplets;

b) a second layer comprising lines approximately 100 microns Wide spaced approximately 300 microns center-to-center along the length of the 2-cm axis, wherein the lines are approximately 200 microns in depth and placed directly above the lines in the first layer;

c) a third layer comprising lines approximately 100 microns wide with approximate 100 micron spacing printed along the 1 cm axis with approximate 100 micron spacing in between with an approximate 200 micron depth, and wherein the lines are printed on top of each of the outside lines in each triplet in the layer below;

d) a second-to-last layer that is the same as the second layer;

e) a layer between the second-to-last layer and the last layer that is the same as the third layer; and f) a last layer that is the same as the first layer.

* * * * *

UNITED STATES PATENT AND TRADEMARK OFFICE
CERTIFICATE OF CORRECTION

PATENT NO. : 6,530,958 B1
DATED : March 11, 2003
INVENTOR(S) : Linda G. Cima and Michael J. Cima It is certified that error appears in the above-identified patent and that said Letters Patent is hereby corrected as shown below:

<u>Title page,</u>
Item [60], Related U.S. Application Data, "Pat. No. 5,510,680" should read
-- Pat. No. 5,518,680 --.

Signed and Sealed this

Fourteenth Day of October, 2003

JAMES E. ROGAN
*Director of the United States Patent and Trademark Office*